United States Patent [19]

Levy et al.

[11] Patent Number: 4,822,802

[45] Date of Patent: Apr. 18, 1989

[54] METHOD OF FENTANLY ADMINISTRATION FOR POSTOPERATIVE PAIN RELIEF

[75] Inventors: Gerhard Levy, Williamsville, N.Y.; Mary Southam, Portola Valley; Marilou S. Powers Cramer, Redwood, both of Calif.

[73] Assignee: ALZA Corporation, Palo Alto, Calif.

[21] Appl. No.: 18,241

[22] Filed: Feb. 24, 1987

[51] Int. Cl.$^4$ .................... A61U 31/44; A61U 31/445
[52] U.S. Cl. .................................... 514/317; 514/349
[58] Field of Search ................................. 514/349, 317

[56] References Cited

U.S. PATENT DOCUMENTS 4,588,580  5/1986  Gale et al. .............................. 424/21

OTHER PUBLICATIONS

Chem. Abst. 104 (1986) 213272t.
Physician's Desk Reference, pp. 1033–1035, 1987 edition.
F. O. Holley et al., "Transdermal Administration of Fentanyl for Postoperative Analgesia," *Anesthesiology*, v. 65 (3A), Sep. 1986.
W. S. Nimmo et al., "Plasma Fentanyl Concentrations After Transdermal or I.V. Infusion of Fentanyl", *Anesthesiology*, v. 65 (3A), Sep. 1986.
D. J. R. Duthie et al., "The Pharmacokinetics of Fentanyl by Constant Rate I.V. Infusion for Pain Relief After Surgery," *Anesthesiology*, V. 63(3A), Sep. 1985.
W. S. Nimmo et al., "Fentanyl by Constant Rate I.V. Infusion for Postoperative Analgesia," *Br. J. Anaesth.*, v. 57, pp. 250–254 (1985).
D. J. R. Duthie et al., "Pharmacokinetics of Fentanyl During Constant Rate I.V. Infusion for the Relief of Pain After Surgery," *Br. J. Anaesth.*, v. 58, pp. 950–956 (1986).
Plezia et al., "Transdermal Therapeutic System (Fentanyl) for Postoperative Pain: An Efficacy, Toxicity, and Pharmacokinetic Trail.", ASA Abstracts, A210, (Sep. 1986), *Anesthesiology*, vol. 65 (3A).
Caplan et al., "Transdermal Delivery of Fentanyl for Postoperative Pain Control", (Sep. 1986), *Anesthesiology*, vol. 65 (3A).
H. Stoeckel et al., "Pharmacokinetics of Fentanyl as a Possible Explanation for Recurrence of Respiratory Depression," *Br. J. Anaesth.* 51, pp. 741–744, (1979).

*Primary Examiner*—Stanley J. Friedman
*Attorney, Agent, or Firm*—Edward L. Mandell; Shelley G. Precivale; Steven F. Stone

[57] ABSTRACT

A method of postoperative pain relief using transdermal delivery of fentanyl or its analgetically effective derivatives preceded by a dose of said material to increase the serum drug levels to steady state more quickly.

8 Claims, No Drawings

4,822,802

METHOD OF FENTANLY ADMINISTRATION FOR POSTOPERATIVE PAIN RELIEF

FIELD OF THE INVENTION

This invention relates to the administration of analgesics. More particularly, this invention relates to the administration of fentanyl and its analgetically effective derivatives for analgetic purposes. Still more particularly, but without limitation thereto, this invention relates to the transdermal administration of such materials supplemented with a bolus dosage thereof.

BACKGROUND OF THE INVENTION

Fentanyl and its analgetically effective derivatives such as sufentanil, carfentanil, lofentanil and affentanil are classified in the art as being extremely potent narcotic analgesics and are used extensively as anesthetics. Fentanyl is described in U.S. Pat. No. 3,164,600 and its use as approved by the FDA in the United States is described in the 1984 Physician's Desk Reference, pages 1027 through 1029 with reference to the drug SUBLIMAZE® manufactured by McNeil Lab for Janssen Pharmaceutica, Inc.

In use, fentanyl is commonly administered as the citrate, either as a bolus injection or infusion or a continuous infusion for the purposes of producing anesthesia. More recently, transdermal delivery of fentanyl and its analgetically effective derivatives has been accomplished and one such transdermal delivery system is disclosed in U.S. Pat. No. 4,588,580, which is incorporated herein by reference. The advantages of transdermal delivery is the ability to continuously deliver the drug at analgetically effective rates over an extended period of time. This system has proven to be successful, as reported by P.M. Plezia, J. Linford, T.H. Kramer, R.P. Iacono, and S.R. Hameroff, in Transdermal Therapeutic System (Fentanyl) for Postoperative Pain: An Efficacy, Toxicity, and Pharmacokinetic Trial, ASA Abstracts, A210, Anesthesiology, vol. 65(3A), (September, 1986).

In use, fentanyl transdermal systems exhibit a delay or "lag time" between the application of the transdermal delivery device and the onset of analgesia. Thus, transdermally administered fentanyl serum concentrations take longer to attain their plateau in comparison to intravenous administration primarily because of the requirement to saturate the drug binding sites in the skin. In effect, the skin beneath the transdermal system acts as a presystemic compartment, delaying the onset of systemic drug absorption. This lag time may present a problem in certain instances where fentanyl is being used to relieve postoperative pain. Similar problems may also occur with the analgetically effective derivatives of fentanyl.

SUMMARY OF THE INVENTION

An object of this invention is to provide an improved method of administration of fentanyl and its analgetically effective derivatives for the relief of postoperative pain.

A further object of this invention is to reduce or eliminate the lag time to onset of analgesia experienced with transdermal delivery of fentanyl and its analgetically effective derivatives.

These and other objects are accomplished by the present invention wherein the transdermal delivery of fentanyl and its analgetically effective derivatives is supplemented with a 100 to 300 μg dosage of fentanyl and its analgetically effective derivatives.

DESCRIPTION OF THE PREFERRED EMBODIMENT

As described in U.S. Pat. No. 4,588,580, incorporated herein by reference, it was found that fentanyl and its derivatives could be delivered transdermally to induce analgesia. To achieve this with fentanyl, administration should be range of from about 10 to 300 μg/hr, with the preferable analgetically effective rate being within the range of about 25 to 150 μg/hr. The effective rates for the other derivatives will vary depending on potency as described in the above referenced patent. Transdermal administration is maintained at least until the patient recovers from anesthesia, with a 1 to 3 day regimen being typical. Transdermal fentanyl delivery devices can be provided having varying effective durations, typically form 1 to 7 days. If analgesis is required for a time period greater than the duration of the device, continuous analgesia can be obtained by removing the depleted device and applying a fresh device preferably at a different location on the skin.

When fentanyl is administered as described in U.S. Pat.No. 4,588,580, certain patients exhibited a lag time of about 12 hours before analgetically effective serum drug levels were achieved. This was too long to achieve analgesia when recovering from anesthesia after short duration surgical procedures. Part of this lag time can be taken care of according to our invention by placing the transdermal system on the patient prior to anesthesia and surgery. This, coupled with a 100 to 300 μg dose of fentanyl given at the induction of anesthesia provides analgetically effective serum drug levels when pain relief is needed, even for short duration procedures. In this manner, transdermal fentanyl administration functions as maintenance therapy. The dosage may be higher than 300 μg if necessary, but for most situations a 100-300 μg range is suitable. This dose will be different for other derivatives based upon their relative potency as indicated in Table 1.

TABLE 1

| DRUG | RELATIVE POTENCY (Fentanyl = 1) |
| --- | --- |
| (1) Fentanyl | 1 |
| (2) Sulfentanyl | 15 |
| (3) Carfentanyl | 34 |
| (4) Lofentanyl | 15 |
| (5) Alfentanyl | 0.25 |

The preferred embodiment of this invention comprises an intravenous 100 to 300 μg dose of fentanyl or its analgetically effective derivatives such as sufentanil, carfentanil, lofentanil and alfentanil. for use in conjunction with a general anesthetic such as nitrous oxide. Alternately the 100 to 300 μg dose may be epidural when anesthesia is by spinal injection. In the latter instance, the dose used can be a low as 50 μg. A typical dosage composition is like that commercially available under the trademark SUBLIMAZE® manufactured by McNeil Lab for Janssen Pharmaceutica, Inc.

A serum concentration of fentanyl within the range of 1 to 3 ng/ml provides effective analgesia. Because fentanyl is rapidly cleared from the body, when used in these ranges the serum levels from the initial dosage are dropping off as the serum levels from the transdermal administration are increasing.

The following table shows suitable combinations of bolus dosages and transdermal delivery rates, it being recognized that there are variations from patient to patient and titration to individual patient requirements is recommended.

TABLE II

| Dose, μg | Transdermal Rate, μg/hr |
|---|---|
| 100 | 50 |
| 100–200 | 75 |
| 200–300 | 100 |

It is preferable to vary the time of placement of the transdermal system, rather than increase the dosage of fentanyl at the induction of anesthesia. Effective serum fentanyl concentrations can be obtained by applying the transdermal system no later than the induction of anesthesia, ie. either simultaneously or before induction of anesthesia . This early placement will provide the plasma level needed while avoiding unacceptable respiratory depression.

The full scope of this invention can be best understood in light of the following example.

EXAMPLE I

Ten adult patients undergoing elective shoulder surgery with regional anesthetic were given a 100 μg IV fentanyl dose in conjunction with a fentanyl transdermal system capable of delivering 75 μg/hr, placed on the anterior chest. The system was left in place for 24 hours.

The following table provides the average hourly requirement for supplemental morphine in patients using the dose/transdermal fentanyl, compared with a similar group of shoulder surgery patients who only used intravenous morphine by patient-controlled infusion. Patients receiving the dose/transdermal fentanyl required significantly less morphine during the period of time that the transdermal system was in place, and over the first 48 hours of postoperative narcotic use

TABLE III

| | Postoperative Morphine Requirements (mg morphine/patient/hr) | |
|---|---|---|
| Time | Transdermal fentanyl | IV Morphine Only |
| 0–12 hrs | 0.78 + 0.6 | 1.69 + 1.0 |
| 13–24 hrs | 0.17 + 0.3 | 1.51 + 1.1 |
| 25–36 hrs | 0.92 + 0.8 | 1.32 + 1.0 |
| 37–48 hrs | 1.00 + 0.7 | 0.47 + 0.5 |
| Overall | 0.70 + 0.4 | 1.35 + 0.9 |

This data was reported by R.A. Caplan, L.B. Ready, G.L. Olsson and M.L. Nessley, "Transdermal Delivery of Fentanyl for Postoperative Pain Control", *Anesthesiology*, vol. 65(3A), (September 1986), said research being conducted under the sponsorship and according to protocols provided by Alza Corporation (Palo Alto, CA).

This invention has been described in detail with particular reference to certain preferred embodiments thereof, but it will be understood that variations and modifications can be effected within the spirit and scope of the invention.

What is claimed is:

1. A method for inducing and maintaining postoperative analgesia in a surgical patient which comprises:
   (a) administering to said patient a 100–300 μg dosage of a material selected from the group consisting of fentanyl, sufentanil, carfentanil, lofentanil and alfentanil, at the induction of anesthesia; and
   (b) placing a transdermal delivery device adapted to continuously transdermally administer a material selected from the group consisting of fentanyl, sufentanil, carfentanil, lofentanil and alfentanil, at an analgetically effective rate, on said patient no later than the induction of anesthesia; and
   (c) continuing the transdermal administration of said material at said rate by maintaining said device on said patient at least until said patient has recovered from anesthesia;
   wherein said material is administered internally and transdermally for analgesia.

2. The method of claim 1 wherein said material is fentanyl and said analgetically effective rate is in the range of about 25 to 150 μg/hr.

3. The method of claim 2 wherein said dosage is about 100 μg and said analgetically effective rate is about 50 μg/hr.

4. The method of claim 2 wherein said dosage is about 100–200 μg and said analgetically effective rate is about 75 μg/hr.

5. The method of claim 2 wherein said dosage is about 200–300 μg and said analgetically effective rate is about 100 μg/hr.

6. The method of claim 1 wherein said placing step is simultaneous with the induction of anesthesia.

7. The method of claim 1 wherein said placing step is before the induction of anesthesia.

8. The method of claim 1 wherein said administering step is done intravenously.

* * * * *

UNITED STATES PATENT AND TRADEMARK OFFICE
CERTIFICATE OF CORRECTION

PATENT NO. : 4,822,802
DATED : April 18, 1989
INVENTOR(S) : Levy et al.

It is certified that error appears in the above-identified patent and that said Letters Patent is hereby corrected as shown below:

Title page:

Item [54] in the title "Fentanlv" should be -- Fentanyl --;

Item [57] in the Abstract, line 3, after a; insert -- 100 to 300 µg --; Table I, Column 2, lines 47-50 correct the misspelling of the words so that Table I reads as follows:

TABLE I

| DRUG | RELATIVE POTENCY (Fentanyl = 1) |
|---|---|
| (1) Fentanyl | 1 |
| (2) Sulfentanil | 15 |
| (3) Carfentanil | 34 |
| (4) Lofentanil | 15 |
| (5) Alfentanil | 0.25 |

Signed and Sealed this

Twenty-third Day of January, 1990

Attest:

JEFFREY M. SAMUELS

Attesting Officer  Acting Commissioner of Patents and Trademarks